US007625865B2

(12) United States Patent
Colombo et al.

(10) Patent No.: US 7,625,865 B2
(45) Date of Patent: Dec. 1, 2009

(54) INSULIN HIGHLY RESPIRABLE MICROPARTICLES

(75) Inventors: Paolo Colombo, Parma (IT); Stefano Cagnani, Settima Di Gossolengo (IT); Paolo Ventura, Piacenza (IT)

(73) Assignee: Universita Degli Studi Di Parma, Parma (IT)

( * ) Notice: Subject to any disclaimer, the term of this patent is extended or adjusted under 35 U.S.C. 154(b) by 236 days.

(21) Appl. No.: 10/593,861

(22) PCT Filed: Mar. 26, 2004

(86) PCT No.: PCT/EP2004/050371

§ 371 (c)(1), (2), (4) Date: Sep. 22, 2006

(87) PCT Pub. No.: WO2005/092301

PCT Pub. Date: Oct. 6, 2005

(65) Prior Publication Data

US 2007/0154404 A1 Jul. 5, 2007

(51) Int. Cl.
*A61K 38/28* (2006.01)
*A61K 51/12* (2006.01)

(52) U.S. Cl. .......................... 514/3; 530/303; 424/1.33

(58) Field of Classification Search ...................... None
See application file for complete search history.

(56) References Cited

U.S. PATENT DOCUMENTS

| | | | | |
|---|---|---|---|---|
| 3,921,637 | A | 11/1975 | Annette et al. | |
| 4,338,931 | A | 7/1982 | Cavazza | |
| 5,320,094 | A | 6/1994 | Laube et al. | |
| 6,306,440 | B1 | 10/2001 | Baeckstroem et al. | |
| 6,582,728 | B1 | 6/2003 | Platz et al. | |
| 2002/0052310 | A1* | 5/2002 | Edwards et al. | 514/2 |
| 2003/0165436 | A1* | 9/2003 | Staniforth et al. | 424/46 |

FOREIGN PATENT DOCUMENTS

| | | |
|---|---|---|
| EP | 0467172 | 1/1992 |
| EP | 0505966 | 9/1992 |
| EP | 0520748 | 12/1992 |
| EP | 0655237 | 5/1995 |
| WO | WO 88/04556 | 6/1988 |
| WO | WO 90/07351 | 7/1990 |
| WO | WO 90/09780 | 9/1990 |
| WO | WO 91/02545 | 3/1991 |
| WO | WO 93/02712 | 2/1993 |
| WO | WO 95/24183 | 9/1995 |
| WO | WO 99/55362 | 11/1999 |
| WO | WO 99/66903 | 12/1999 |
| WO | WO 00/00176 | 1/2000 |
| WO | WO 01/93837 | 12/2001 |
| WO | WO 02/053190 | 7/2002 |

OTHER PUBLICATIONS

Stahl, et al., 2002, International Journal of Pharmaceutics, 233, 227-237.*
International Search Report.
Büchi, Labortechnik AG, Flawil, Switzerland (Spec.).
Forbes et al., "Water Vapor Sorption Studies . . . ", Journal of Pharmaceutical Sciences, 1998, vol. 87, No. 11, pp. 1316-1321. (ISR).
Todo et al., "Effect of additives on insulin absorption from . . . ", International Journal of Pharmaceutics, 2001, vol. 220, No. 1-2, pp. 101-110. (ISR).
Quaglia F et al., "Feeding liquid, non-ionic surfactant . . . ", Journal of Controlled Release, 2003, vol. 86, No. 2-3, pp. 267-278. (ISR).
A.L. Jones, "Proceedings of the third European . . . ", 1987, vol. 2, pp. 143-149. (Spec).
Colthorpe et al., Pharmaceutical Research, 1992, vol. 9, pp. 764-768. (Spec).
Komoda, F., J. Phar. Sci., 1994, vol. 83, pp. 863-867. (Spec).
Diabetes Care, 1990, vol. 13, pp. 953-954. (Spec).
Lee, S., J. Phar. Sci., 1976, vol. 65, pp. 567-572. (Spec).
Patton, J.S., "Inhaled Insulin", Adv. Drug Del. Rev. 35, 1999, pp. 235-247. (Spec).
Langer, R. et al., J. App. Physiol., 1998, vol. 85, pp. 379-385. (Spec).
Nagai, T., J. Contr. Rel., 1984, vol. 1, pp. 15-22. (Spec).
Rydén, L., Int. J. Pharm. 1982, vol. 83, pp. 1-10. (Spec).

European Pharamcopeia, $4^{th}$ Edition, <2.9.18> p. 216. (Spec), Jan. 2002.

(Continued)

*Primary Examiner*—Andrew D Kosar
*Assistant Examiner*—Satyanarayana R Gudibande
(74) *Attorney, Agent, or Firm*—Collard & Roe, P.C.

(57) ABSTRACT

The invention describes novel dried powders of peptide therapeutic agent useful for producing highly respirable aerosols and the methods for their manufacture. Insulin is the peptide therapeutic agent in the preferred embodiment. The powders of insulin prepared for pulmonary administration are characterized by the peculiar structure and shape of the microparticles that allow the powder to flow and to be easy aerosolized. Typical dry powder of insulin described in this patent show corrugated, nonagglomerated microparticles with a low tapped density. The mean geometric diameter (particle size) ranges between 1.0 and 10.0 micron and the mass median aerodynamic diameter (MMAD) ranges between 1.0 and 4.0 micron. These insulin pulmonary powders exhibit in vitro a very high respirable fraction (>75%).

5 Claims, 1 Drawing Sheet

OTHER PUBLICATIONS

A.L. Jones et al., *"An Investigation of the Pulmonary Absorption of Insulin in the Rat."* "Proceedings of the third European . . . " 1987, vol. 2, pp. 143-149. (Spec).

Colthorpe et al., *"The Pharmacokinetics of Pulmonary-Delivered Insulin: A Comparison of Intratracheal and Aerosol Administration to the Rabbit."* Pharmaceutical Research, 1992, vol. 9, pp. 764-768. (Spec).

Komoda, F. et al., *"Intratracheal Delivery of Peptide and Protein Agents: Absorption from Solution and Dry Powder by Rat Lung."* J. Phar. Sci., 1994, vol. 83, pp. 863-867. (Spec).

*"Monomeric Insulins and Their Experimental and Clinical Implications."* Diabetes Care, 1990, vol. 13, pp. 953-954. (Spec).

Lee, S. et al., *"Development of an Aerosol Dosage Form Containing Insulin."* J. Phar. Sci., 1976, vol. 65, pp. 567-572. (Spec).

Patton, J.S. *"Inhaled Insulin"*, Advanced Drug Delivery Reviews 35, 1999, pp. 235-247. (Spec).

Edwards, D.A. et al., *"Recent advances in pulmonary drug delivery using large, porous inhaled particles."* J. App. Physiol., 1998, vol. 85, pp. 379-385. (Spec).

Nagai, T. et al., *"Powder dosage form of insulin for nasal administration."* J. Contr. Rel., 1984, vol. 1, pp. 15-22. (Spec).

Rydén, L. et al., *"Effect of polymers and microspheres on the nasal absorption of insulin in rats."* Int. J. Pharm. 1992, vol. 83, pp. 1-10. (Spec).

European Pharamcopeia, $4^{th}$ Edition, "Preparations for inhalations: Procedure for powder inhalers." <2.9.18> p. 216-217. (Spec), 2002.

European Pharamcopeia, $4^{th}$ Edition, "Insulin, Bovine; Insulin, Human . . . " pp. 1368-1381, 2002.

\* cited by examiner

FIG 1. Pure insulin microparicles from acetic acidic solution pH 3.27
FIG 2: Pure insulin microparticles from HCl acidic solution pH 4.44

INSULIN HIGHLY RESPIRABLE MICROPARTICLES

CROSS REFERENCE TO RELATED APPLICATIONS

Applicants claim priority under 35 U.S.C. §365 of PCT/EP2004/050371 filed Mar. 26, 2004. The international application under PCT article 21(2) was published in English.

FIELD OF THE INVENTION

It is known that certain drugs delivered to the lung are readily absorbed through the alveolar region into the blood circulation. Pulmonary delivery is a promising alternative route in particular for the administration of macromolecules such as proteins, polypeptides and nucleic acids, which are exclusively delivered by injection. Lung delivery is useful for both systemic and local therapeutic activity. Pulmonary drug delivery has to be achieved by producing an aerosol of the active. Aerosols can be generated by different methods, including liquid nebulizers, pressurized metered dose inhalers (MDI) and dry powders inhalers (DPI). The CFC propellant phase out caused aerosol based MDI to loose favor while increasing interest focused on dry powder devices. In such devices, drugs are formulated as respirable dry powder obtained by freeze-drying or spray-drying or other suitable techniques. The drugs may be combined with safe excipients in order to improve their respirability, stability and flowability.

Typical techniques for delivering dry powder formulations via a DPI are loading one dose of the drug in a hard gelatin capsule or aluminum blister or to load the device with multiple doses leaving to the device to sample the amount required. This step requires powders having favorable properties of flow and packing. These properties are typical of the coarse powders. Upon patient inspiration the air flowing through the device penetrates into the drug reservoir and aerosolizes the powder dose. This second step requires micronized powders having particle with size, shape and density useful for aerosolization.

The ability to deliver a drug to the alveolar region of the respiratory tract, where the absorption takes place, is problematic under different points of view. In details, a powder must be capable to overcome the paradox to be fine for aerosolization and lung deposition but at the same time to be coarse for the dosing in the device of the amount to be administered. Firstly, the dose of drug must be accurately metered and this relies on the packing and flow properties of the powder and characteristics of device for administration. Secondly, the powder to be inhaled must be easily dispersed in order to assure the generation of respirable aerosol and this relies on powder size, shape and density. A solution for these two contradictory aspects is the object of this patent.

DESCRIPTION OF RELEVANT LITERATURE

The delivery of insulin to the lung has been proposed since its discovery. The simplest method to deliver insulin to the lung in preclinical studies was by direct intra-tracheal instillation of an aqueous formulation. In this case, distribution in the lung tends to be localized and uneven than that seen after aerosol administration, resulting in small surface area available for the absorption. A. L. Jones (Proceedings of the third European congress of Biopharmaceutics and Pharmacokinetics, Vol 2, page 143-149) in 1987 reported a rapid absorption of insulin in rats. P. Colthorpe and S. Farr in 1992 (Pharmaceutical Research, 9: 764-768) using pharmaco-scintigraphy compared the deposition and absorption of the direct instillation and the nebulization of an acidic insulin solution. He elegantly demonstrated that the absorbed fraction for aerosolized insulin was 10 fold greater than instilled insulin. This provides a clear proof how the mode of administration profoundly affects the fate of pulmonary delivery.

Using intratracheal instillation, the effect of formulation related variables on the extent of pulmonary insulin absorption has also been investigated, including osmolarity, viscosity and solution pH. According to F. Komoda (J. Pharm. Sci. 1994, 83, 863-867) insulin formulation at pH 3 showed greater bioavalability than those at pH 7 after intratracheal instillation. They explained the result by the inhibition of insulin association in the lower pH formulation. Insulin exists as monomer, dimer and exhamer. Dimers and exhamers come from aggregation of the monomeric form and the relative percentage in solution of three forms depends on pH and concentration of the hormone. It is known that insulin self-aggregation affects its diffusive transport across biological membrane (Diabetes Care 1990,13,953-954).

Many ways have been suggested for aerosolizing insulin in form of solution, dry powders and even suspension of liposomes. Metered dose inhalers and Dry powder inhalers are the most recent devices for pulmonary administration of drugs. Metered dose inhalers for delivering crystiline insulin suspended in a propellant have been proposed by S. Lee (J. Pharm. Sci. 1976: 65, 567-572) and a patent exists on this field (U.S. Pat. No. 5,320,094). Dry powder inhalers carrying insulin are also described in the literature (for a complete review: J. S. Patton: Inhaled Insulin, Adv. Drug Del. Rev. 35, 1999, 235-247). Pulmonary delivery of dry powder medicaments in large particle porous particles has been investigated by R. Langer and co-workers (J. App. Physiol. 1998: 85 379-385), and patented (WO 9966903). Other preparations for inhalation which comprise insulin and a substance which enhances the absorption of insulin in the lower respiratory tract, have been proposed in the form of powder preparations suitable for inhalation (U.S. Pat. No. 6,306,440). Intranasal and respiratory delivery of a variety of polypeptides, including insulin, in the presence of an enhancer has been also described by T. Nagai (J. Contr. Rel. 1984: 1, 15-22) and L. Ryden (Int. J. Pharm. 1992: 83, 1-10) and in several patents released worldwide (WO 9302712, WO9102545, WO 9009780, WO 8804556).

The preparation of an amorphous powder containing insulin was illustrated in a patent which described the methods for spray drying polypeptide, polynucleotide and other liable drugs together with a carrier to improve stability of the active after drying (EP 0520748). The first patent on insulin medical aerosol formulation (EP 0655237) discloses the production of an aerosol containing also spray dried insulin intended for lung administration. In the example 4 of the cited patent a powder is prepared from an alcoholic (25% v/v) solution containing the same amount of insulin and lactose and 0.1% soya bean lecithin. In another patent (WO A 9524183) insulin is produced in form of a dried powder from buffered solution at pH 6.7±0.3 containing the hormone. This patent discloses the use of a citrate buffer to dissolve crystal insulin and subsequently the powder is produced by spray drying. Some criticism (refers to WO 00/00176, page 2, line 4-line 6) has been addressed to the experimental section.

Finally, dry powder inhalers are disclosed in several patent applications. Manual pumps (U.S. Pat. No. 3,921,637) or multiple receptacle disks or strips (EP 0467172) are employed. Puncturing gelatin capsule disperser is described in U.S. Pat. No. 4,338,931. A held-pump device has been also patented (WO 09007351). Independently on the device used, the characteristics of drug in powder form are crucial for the efficacy of the preparation.

OBJECT OF THE INVENTION

The object of present invention are pharmaceutical powders of insulin suitable for pulmonary administration intended for the long-term treatment of diabetes, characterized by a structure of the microparticles composing the powder that imparts an elevated respirability, together with favorable flow and packing characteristics. The powders obtained through have been produced by spray drying in never explored conditions of manufacturing, in particular at pH lower than the isoelectric point of insulin. The acidic pH used for particle preparation would allow to obtain higher absorption as F. Komoda previoulsy demonstrated.

The pulmonary powders of insulin object of this patent are characterized by structure and shape of the constituent microparticles defined corrugated or raisin like, completely different from the insulin microcrystal structure. These pulmonary powders of insulin show a flow and packing characteristics that allow them to be directly introduced in the reservoir of DPI delivery systems. More relevant is the fact that the respirability of the powders having these properties is higher that the usual values described in literature. In fact, the fraction of respirable particles composing the insulin aerosol produced with the powders here described ranged between 83.9% and 90.4%, whereas common values range between 20-40%.

This respirability has been assessed using the Andersen Cascade Impactor as described in the European Pharmacopeia (4th Edition, <2.9.18> page 216). This apparatus is used to determine the fine particles of an aerosol cloud, generated by preparations for inhalation, and allows the measure of the mass of drug less than a particular aerodynamic particle size. The mass of drug having aerodynamic diameter lower than 5 μm is generally considered as "respirable", even though the optimal size for alveolar deposition is in the range 5-2 micron.

The manufacturing procedures described in this patent provide the production of fine powders in which more than 90% of particles have dimensions less than 9 microns as volume diameter. The method for preparing said formulation allows high percentage of pharmaceutical activity of the powder to be manufactured.

Moreover, the dry powder exhibits adequate chemical and physical stability. In the background art the insulin solutions to be spray-dried are reported to have a pH near the neutrality obtained by using citrate buffer (pH 6.7±0.3, WO-A-95/24183) or above neutral (WO 00/00176). Insulin for pulmonary therapy in patent WO-A-95/24183 was declared as prepared by spray drying solutions in physiologically acceptable buffer such as citrate buffer at pH between 2.0-9.0, but the powder described in the example was made by spray drying a solution at pH 6.7±0.3. In patent WO 00/00176 the spray drying of a true solution over the isoelectric point of insulin was described.

The present invention is based on the surprising discovery that the spray drying of clear, concentrated, aqueous solutions of insulin having pH lower than the isoelectric point of the hormone (5.4), produces very high respirable dry powders. These powders can be obtained from un-buffered or volatile buffer solutions and were never prepared before. The spray drying of insulin solution under the isoelectric point and therefore, in acidic conditions and without the use of permanent buffering agents, was not previously considered likely for stability and respirability reasons. On the contrary, insulin microparticles produced by spray drying acidic solutions of the hormone resulted in powders particularly suitable for lung administration, because they exhibit a high respirable dose. In addition, the stability was acceptable in refrigerated conditions but, when the powder was manufactured from a solution in acetic acid (volatile buffer), the stability resulted surprisingly very high also in normal conditions. Since no permanent buffers were used, it is also expected that these powders inhaled at the therapeutic doses do no modify the alveolar surfactant pH.

As described in previous patent (WO 00/00176) concerning insulin formulations obtained by spray drying, the neutralisation procedure of insulin solutions to pH above 7.0 results in the production of microparticles with "dimpled surface that may be beneficial" in term of respirability. We reproduced these particles made at pH 7.45 in order to focus the "dimple" shape. The procedure applied is the one described in the WO 00/00176 patent. The microparticles obtained according to the present patent are much more than dimpled since they are corrugated or raisin like (FIGS. 1 and 2). In addition, they are non-cohesive with favourable aerodynamic size and density characteristics.

Similar shapes were observed independently of the acids employed for the preparation of insulin solutions. However, we unexpectedly discovered that when the volatile organic acetic acid is used to dissolve insulin, powders obtained by spray drying from these low pH solutions have lost acidity. In fact, the dissolution of these powders in distilled degassed water gives rise to a solution having pH higher than the value of the original solution. This fact made this powder chemically very stable during storage.

Therefore, the novelty of the powders described in this patent is based on the finding that the peculiar corrugated microparticles obtained by spray-drying insulin acidic solution are micronized, free flowing and with low tapped density. The microparticles are essentially amorphous and characterized by a shape defined corrugated or raisin like. This particle shape makes the powders not cohesive since the microparticles maintain their individuality and do not agglomerate. In addition, they show substantially no losses of activity if stored in refrigerated conditions, but when they are prepared from acetic acid, the insulin powders are very stable also at room conditions (25° C.). In particular, we surprisingly discover that the acetic acid solution of insulin at pH 3.3 after spray drying gave rise to a powder that re-dissolved in distilled degassed water at 1 mg/ml showed a pH of 6.4. Surprising this powder shows a superior stability at 25° C. allowing the preparation to be used and dispensed at room conditions, in comparison with insulin spray dried powders prepared with HCl that must be stored at refrigerated conditions.

Differently from the common technique, such spray dried powders characterized a peculiar insulin particle shape, are produced from clear, volatile buffer or un-buffered solutions having acidic pH values between 3.0-4.5, lower than the isolelectric point of insulin. The use of acidic solutions avoids the risk of precipitation induced by increasing the pH above insulin isoelectric point up to neutrality, but more interestingly provides a structure to dried product that surprisingly is very useful for the aerosolization. In fact, these powders other than to be micronized, are not cohesive, quite free flowing and easy meterable in the DPI. These physical properties, together with the favourable aerodynamic behaviour due to the size, shape and density of the particles, determine an unexpected and surprisingly high respirability.

Finally, the powders contain residual moisture enough to prevent excessive degradation and they can be stored at normal humidity and temperature conditions when prepared from volatile acetic acid.

BRIEF DESCRIPTION OF THE DRAWINGS

FIG. 1 shows pure insulin microparticles from acetic acid solution pH 3.27 in accordance with the invention; and FIG. 2 shows pure insulin microparticles from HCl acidic solution pH 4.44 in accordance with the invention.

FORMULATION ASSAY

The activity of all formulations has been estimated by HPLC. According to the official monographs for "Insulin preparations" (USP 26 and European Pharmacopoeia 4$^{th}$ Edition, page. 1368-1381) HPLC performed in different conditions gives information about potency (according USP 26, potency is evaluated in comparison to a certified standard, test described under "ASSAY"), purity (quantification of the "related proteins") and about the presence of covalent aggregation (called "impurities with molecular masses greater than that of insulin"), both in European Pharmacopoeia 4$^{th}$ Edition.

Pharmacopoeias limits and specifications for the insulin preparations are: A21 desamido not more than 5% of total area of peaks, other not more than 6%. Impurities with molecular masses greater than that of insulin: not more than 2% of total area of peaks.

Aerodynamic diameter was assessed using the Andersen Cascade Impactor. The percentage of mass less than the stated aerodynamic diameter versus aerodynamic diameter is then plotted on a log probability paper (USP 26 page 2123). Respirability of the described formulations is derived from the data plotted as described above considering the mass less than 5 microns as respirable. Packing properties have been studied using tap density measurements. According to the official monograph, tap densities has been evaluated after 1250 taps (USP 26) employing a 10±0.05 ml cylinder filled with the powder.

DESCRIPTION OF THE INVENTION

The microparticles of this invention contain drug substantially free of excipients, but in certain conditions mixture of drug and diluent such as mannitol can be used. Substantially free of excipients means that the microparticles of the invention can include process-linked component as hydrochloric acid or acetic acid and eventually their sodium salts in case of pH adjustement up to about 10% of the total solids. The main advantage of the use of substantially excipient-free formulations is that each dose can contain a large amount of the active. Buffer salts like citrate are not necessary both for solubility and stability of the microparticles described under the invention. In all previous patents insulin final solutions for spray drying are reported to have a pH near the neutrality using citrate buffer (6.7±0.3, WO-A-95/24183) or above neutral (WO 00/00176). The procedure at pH 6.7 did not allow the microparticles to be produced from a clear solution of insulin and from the clear solution above the neutrality the particles had a surface smooth or "dimpled", morphological characteristics, considered as beneficial for inhalation. Nevertheless, the use of mild acidic solutions leads to reproducible production of corrugated or raisin like microparticles, without affecting the insulin stability if properly stored.

The solutions of insulin are spray dried in a conventional spray drying apparatus; even rotary atomization, pressure atomization and two-fluid atomization can be employed as spraying process. No particular restrictions are placed on the gas used to dry the sprayed materials. Filtered air is used in the manufacturing methods described below. The temperature of the inlet of the gas used to dry the sprayed materials should be chosen so that it does not cause degradation of the active. The range may vary between 50° C. and 200° C. The temperature of the outlet gas used may vary between 30° and 100° C., preferably in the range 40° C. and 60° C. This has been found to affect more than the inlet temperature set up the degree of degradation of the dried product. The fact that inlet and outlet temperature above 50° C. can be used has been noted and reported (U.S. Pat. No. 6,582,728). Insulin solutions were prepared by dissolving from 5 to 20 mg of the hormone per milliliter in $10^{-2}$ M hydrochloric acid solutions or 0.4M diluted acetic acid solutions (pH 2.6), diluting with distilled water and adding if necessary an adequate amount of NaOH solution to pH between 3.0 and 4.5, in any case avoiding insulin precipitation. Excipients such as polyalcohols can be added before pH correction. A Mini Spray Drier Buchi, model 191 (Buchi, Labortechnik AG, Flawil, Switzerland) equipment was used. The inlet air (drying gas) had initially, before heating, a relative humidity of about 30-70%. The nozzle was provided with an orifice of 0.7 or 1.0 mm internal diameter. The atomizing gas was filtered compressed air. The spray drier was equipped with a standard cyclone. The used range of the spray drying parameters was: feed flow rate 180-360 ml/h; nozzle gas flow rate 500-800 I/h; inlet air temperature <140° C., producing an outlet temperature of 40-60° C.; aspirator capacity ≦35 $m^3$/h (100% setting). The selected parameter range allowed to obtain an original and new powder with good flow and packing properties, having particle size, shape and density in the respiratory range and with a respirable fraction higher than 80%, with a moisture content in the range of 2 to 8% and a pH of reconstituted solution near neutrality when the acidic solution to spray dry was made with acetic acid, thus preventing insulin degradation.

EXAMPLES

According to the object of the invention, the following dispersible dry powder formulations were prepared as described. All formulations meet the strict specifications for content and purity required for pharmaceutical products.

Example 1

A) Formulation.

2550 mg of highly purified bovine insulin was dissolved in 200 ml of aqueous $10^{-2}$M hydrochloric acid. The solution was added with 100 ml of distilled water and then with 450 mg of mannitol under stirring to give a final solid concentration of 10 mg per ml (8.5 mg bovine insulin per ml). The pH of the clear solution was adjusted to 4.35 using NaOH 0.1 N dropwise.

B) Spray Drying.

This solution was filtered and was spray dried using a Mini spray drier Büchi, model 191 (Büchi, Labortechnik AG, Flawil, Switzerland) under the following process conditions: feed flow rate 195 ml/h; nozzle gas flow rate 600 nl/h; atomizing nozzle diameter 1.0 mm; inlet air temperature 120° C., producing an outlet temperature of 42° C.; aspirator capacity 100% setting. The yield was about 60%.

C) Characterization.

The collected powders were assayed by HPLC for covalent aggregation and degradation products (A21 desamido insulin) according to the European Pharmacopeia 4 (pag. 1368-1381), by Scanning Electron Microscopy (SEM) for morphology investigations, by laser diffraction for particle size distribution and Andersen Cascade Impactor for respirable fraction evaluation.

The potency was 22.6 UI/mg, the related proteins were 0.5% and the impurities with molecular mass greater than insulin were 0.55%. The powder contained approximately 5.8% moisture. The particle size distribution of the powder was determined to be 2.33 ($d_{10}$), 3.62 ($d_{50}$) and 5.68 ($d_{90}$) microns as volume diameter. The respirability (mass less than 5 microns) derived from Andersen Cascade Impactor data was high as 85.7%. The packing properties measured as tapped density (European. Pharmacopoeia 4 t Edition) was 0.2 g/cm$^3$. The powder dissolved in distilled and degassed water gave rise to a pH of 4.4. Weighed amounts of powder were then placed into separated glass vials and stored at −18° C.,in a refrigerator at 5±3° C. and at room temperature and humidity (25±3° C. and 65±5% RH respectively) and analysed at different times by HPLC for stability.

Example 2

A): Formulation.

975 mg of bovine insulin was dissolved in 95 ml of aqueous diluted acetic acid (pH 2.6). The solution was added with 0.6 ml of NaOH 1 M. The pH of the clear solution was 3.27.

B): Spray drying Process.

This solution was filtered and subsequently spray dried using a Mini spray drier Büchi, model 191 (Büchi, Labortechnik AG, Flawil, Switzerland) under the following process conditions: feed flow rate 200 ml/h; nozzle gas flow rate 500 nl/h; atomizing nozzle diameter 1.0 mm; inlet air temperature 130° C., producing an outlet temperature of 55° C.; aspirator capacity 100% setting. The yield was about 50%.

C) Characterization.

The collected powders were assayed by HPLC for covalent aggregation and degradation products (A21 desamido insulin) again according to the European Pharmacopeia and by the already quoted assays. The potency was 28.9 Ul/mg, the related proteins were 0.6% and the impurities with molecular mass greater than insulin was 0.33%. The particle size distribution was determined to be 4.06 ($d_{10}$), 4.36 ($d_{50}$) and 4.93 ($d_{90}$) microns as volume diameter. The respirability (mass less than 5 microns) derived from Andersen Cascade Impactor data was high as 83.9%. The tapped density, index of packing properties, (Eu.Pham), was 0.1 g/cm$^3$. The powder dissolved in distilled and de-gased water gave rise to a pH of 6.4. Microparticles exhibit a raisin-like shape (FIG. 1).

Example 3

A) Formulation.

1750 mg of highly purified bovine insulin was dissolved in 120 ml of aqueous $10^{-2}$ M hydrochloric acid. The solution was added dropwise with0.0.7 ml of 1 N NaOH to give a final pH of about 4.44. The solution is clear and contains about 15 mg per ml of solids.

B) Spray Drying Process.

This solution was filtered and then spray dried using a Mini spray drier Büchi under the following process conditions: feed flow rate 195 ml/h; nozzle gas flow rate 600 nl/h; atomisng nozzle diameter 1.0 mm; inlet air temperature 120° C., producing an outlet temperature of 46° C.; aspirator capacity 100% setting. The yield was about 55%.

C) Characterization.

The microparticles were assayed by HPLC for covalent aggregation and degradation products (A21 desamido insulin) according to the European Pharmacopoeia, by SEM for morphology investigations, by laser diffraction for particle size distribution and by Andersen Cascade Impactor for respirable fraction evaluation.

The potency was 27.1 Ul/mg, the related proteins were 0.7% and the impurities with molecular mass greater than insulin were 0.4%. The formulation contained approximately 4.7% moisture The particle size distribution was determined to be 3.12 ($d_{10}$), 4.72 ($d_{50}$) and 7.24 ($d_{90}$) microns as volume diameter. The powder dissolved in distilled and degassed water gave rise to a pH of 4.7.

The respirability (mass less than 5 microns) derived from Andersen Cascade Impactor data was high as 90.4%.

Weighed amounts of powder were then placed into separated vials and stored at −18° C., in a refrigerator at 5±3° C. and at room temperature and humidity (25±3° C. and 65±5% RH respectively) and analyzed at different times by HPLC for stability.

The invention claimed is:

1. Microparticles stable and storable at room temperature of insulin, showing a d90 volume diameter lower than 9 μm, 80% of them exhibiting an aerodynamic diameter lower than 5 μm, having corrugated or raisin-like surface and having a moisture content in the range of 2 to 8%, said microparticles having a tapped density lower than 0.2 g/cm$^3$ and being obtained by spray drying an aqueous solution of insulin having an acid pH under the isoelectric point (5.4) of insulin and a concentration of insulin in amounts of from 5 to 100 mg/ml, said aqueous solution being prepared in an unbuffered aqueous solution of acetic acid.

2. Microparticles according to claim 1, wherein insulin is in association with excipients selected from the group consisting of saccharides, polysaccharides, amino acids, phospholipids and polyalcohol.

3. Microparticles according to claim 1 containing insulin in amorphous form.

4. Microparticles according to claim 2, wherein said excipient is mannitol.

5. Pharmaceutical compositions suitable to be inhaled comprising the microparticles according to claim 1.

* * * * *

UNITED STATES PATENT AND TRADEMARK OFFICE
CERTIFICATE OF CORRECTION

PATENT NO. : 7,625,865 B2  Page 1 of 1
APPLICATION NO. : 10/593861
DATED : December 1, 2009
INVENTOR(S) : Colombo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 306 days.

Signed and Sealed this

Second Day of November, 2010

David J. Kappos
*Director of the United States Patent and Trademark Office*